United States Patent [19]

Flora et al.

[11] 4,275,059

[45] Jun. 23, 1981

[54] SALICYLATE ANTI-INFLAMMATORY COMPOSITION

[75] Inventors: Lawrence Flora, Hamilton; Marion D. Francis, Cincinnati, both of Ohio

[73] Assignee: The Procter & Gamble Company, Cincinnati, Ohio

[21] Appl. No.: 929,471

[22] Filed: Jul. 31, 1978

Related U.S. Application Data

[63] Continuation of Ser. No. 782,143, Mar. 28, 1977, abandoned.

[51] Int. Cl.³ .................. A61K 31/60; A61K 31/61; A61K 31/66; A61K 31/615; A61K 31/615
[52] U.S. Cl. .................................. 424/204; 424/230; 424/233; 424/234; 424/235
[58] Field of Search ............... 424/204, 222, 230, 233, 424/234, 235

[56] References Cited

U.S. PATENT DOCUMENTS

| | | | |
|---|---|---|---|
| 3,553,314 | 6/1971 | Francis | 424/204 |
| 3,553,315 | 6/1971 | Francis | 424/204 |
| 3,584,124 | 6/1971 | Francis | 424/204 |
| 3,584,125 | 6/1971 | Francis | 424/204 |
| 3,641,246 | 2/1972 | Francis | 424/204 |
| 3,662,066 | 5/1972 | Francis | 424/204 |
| 3,678,164 | 7/1972 | Francis | 424/204 |
| 3,683,080 | 8/1972 | Francis | 424/204 |
| 4,044,125 | 8/1977 | Walkleng | 424/233 |
| 4,049,803 | 9/1977 | Cotley et al. | 424/233 |

*Primary Examiner*—Stanley J. Friedman
*Attorney, Agent, or Firm*—Steven J. Goldstein; Jerry J. Yetter; Richard C. Witte

[57] ABSTRACT

The anti-inflammatory activity of aspirin and other salicylate-based, anti-inflammatory drugs is enhanced by administration thereof in conjunction with a phosphonate compound such as EHDP or $Cl_2MDP$.

21 Claims, No Drawings

SALICYLATE ANTI-INFLAMMATORY COMPOSITION

This is a continuation, of application Ser. No. 782,143 filed Mar. 28, 1977, now abandoned.

BACKGROUND OF THE INVENTION

The present invention relates to compositions and processes for relieving inflammation. More specifically, phosphonate compounds are administered in conjunction with well-recognized, salicylate-based, anti-inflammatory agents such as aspirin, and the like, to treat undesirable inflammation of body tissues.

Inflammation, or the "inflammatory response", is the result of complex interconnected physiological events, including increased vascular permeability, fluid accumulation, and the migration of a changing population of inflammatory cells into the inflamed area. The clinical manifestations of inflammation include swelling (edema), increased local temperature, erythema, and pain. The inflammatory response can be triggered by any of a number of causative factors, including certain bacteria, radiation, hypersensitivity to chemical agents, arthritis-like conditions, and the like. The inflammatory response is generally believed to be a primary defense mechanism in the body, but, unchecked, can become excessive and can result in functional impairment.

The use of salicylates, especially aspirin and aspirin derivatives, to combat inflammation and attendant pain is accepted medical practice. Salicylates are commonly employed to relieve pain and inflammation associated with, for example, bursitis, arthritis, and the like.

The use of pharmacologically-active phosphonate compounds to check the anomalous mobilization and deposition of calcium phosphate salts in the body, e.g., as a treatment for arthritis, is known.

By the present invention, pharmacologically active phosphonate compounds are administered in conjunction with aspirin or other salicylate-based anti-inflammatory agents to provide an improved therapy for pain and inflammation, especially in the treatment of arthritis, and like diseases.

RELATED REFERENCES

The salicylates are widely used in the treatment of rheumatic and arthritic disorders: REPORT ON RHEUMATIC DISEASES No. 33, London, The Arthritis and Rheumatism Council, 1968. Reviews of the control of pain in rheumatic diseases appear in the *British Medical Journal*, iii/1968, 635, by F. D. Hart; *Prescribers' Journal*, 1969, 8, 120, by E. M. Ansell; and *Practitioner*, 1970, 205, 597, by F. D. Hart.

Analgesic abuse is often noted in patients with chronic gastrointestinal or renal disease. Many such patients are in the habit of taking analgesics for prolonged periods and usually in excessive doses; *Clin. Med.*, 1968, 75 (Aug.) 19; *Lancet*, ii/1969, 1233. A listing of references relating to salicylate analgesics and contraindications appears in Martindale, THE EXTRA PHARMACOPOEIA, 26th Ed., The Pharmaceutical Press, London, pp. 221–227.

The phosphonate compounds used in the practice of this invention are reported in the literature as being useful in the treatment of anomalous mobilization and deposition of calcium phosphate salts (bone mineral) in humans and other animals. See especially the U.S. Pat. Nos. of M. D. Francis: 3,683,080, granted Aug. 8, 1972; 3,678,164 granted July 18, 1972; 3,662,066, granted May 9, 1972; 3,553,314, granted Jan. 5, 1971; 3,553,315, granted Jan. 5, 1971; 3,584,124, granted June 8, 1971; 3,584,125, granted June 8, 1971; and 3,641,246, granted Feb. 8, 1972.

The article by Francis, Flora and King, entitled "The Effects of Disodium Ethane-1-Hydroxy-1,1-Diphosphonate on Adjuvant Induced Arthritis in Rats", appearing in *Calc. Tiss. Res.* 9, 109–121 (1972) mentions the use of phosphonates to inhibit inflammatory erosion of cartilage in rats.

The copending application of L. Flora, entitled PHARMACEUTICAL COMPOSITION, Ser. No. 705,650, filed July 15, 1976, discloses the topical administration of phosphonate compounds of the type used herein to humans to alleviate pathological calcification.

By the present invention, the anti-inflammatory activity of salicylate compounds is potentiated by phosphonate compounds. Thus, the invention encompasses a means whereby a patient afflicted with tissue inflammation can secure relief without risking analgesic abuse due to over-use of salicylates.

SUMMARY OF THE INVENTION

The present invention encompasses compositions and means for treating pain and inflammation in animal tissues, especially in humans. The invention provides effective drug combination compositions and therapy, and is based on the use of pharmacologically-active phosphonate compounds in combination with salicylate-based anti-inflammatory agents such as aspirin.

The compositions of this invention comprise an effective amount of a salicylate-based anti-inflammatory compound in combination with an effective amount of a phosphonate compound. The compounds act in concert to provide improved anti-inflammatory benefits.

The invention also encompasses treatment regimens comprising administering an effective amount of the salicylate-based anti-inflammatory agent and an effective amount of a phosphonate compound to an animal, especially a human, suffering from tissue inflammation.

Preferred salicylate-based treatment regimens and compositions herein employ acetylsalicylic acid (aspirin), or the pharmaceutically-acceptable salts thereof, and, as the phosphonate compound, a member selected from the group consisting of ethane-1-hydroxy-1,1-diphosphonic acid, and the pharmaceutically-acceptable salts and esters thereof, and dichloromethanediphosphonic acid, and the pharmaceutically-acceptable salts and esters thereof. The dichloromethanediphosphonates are surprisingly effective at low usage levels, and are especially preferred herein. Mixtures of salicylates can be used, as can mixtures of phosphonates.

DETAILED DESCRIPTION OF THE INVENTION

The compositions and treatment regimens of this invention employ: (1) a safe and effective amount of a pharmaceutically-acceptable salicylate-based anti-inflammatory compound; and (2) a safe and effective amount of a pharmaceutically-acceptable phosphonate compound. These compounds are administered to alleviate inflammation in a patient in need of such treatment.

By "safe and effective amount of salicylate-based anti-inflammatory compound" herein is meant sufficient salicylate compound to alleviate tissue inflammation, at a reasonable benefit/risk ratio attendant with any medical treatment, when used in the manner of this invention. Within the scope of sound medical judgment, the dosage of salicylate compound will vary with the particular condition being treated, the severity of the condition, the duration of the treatment, and the specific salicylate and phosphonate compounds employed.

By "safe and effective amount of phosphonate compound" herein is meant a sufficient amount of the phosphonate compound to potentiate the anti-inflammatory response over that elicited by the salicylate compound, alone, at a reasonable benefit/risk ratio attendant with any medical treatment. Within the scope of sound medical judgment, the dosage of phosphonate will vary with the particular condition being treated, the severity of the condition, the duration of the treatment, and the specific phosphonate and salicylate compounds employed.

By "pharmaceutically-acceptable" herein is meant that the drug compounds and other ingredients used in the present compositions and processes are suitable for use in contact with the tissues of humans and lower animals without undue toxicity, irritation, allergic response, and the like, commensurate with a reasonable benefit/risk ratio.

The term "administration" of the compounds and compositions herein includes systemic use, as by injection (especially parenterally), intravenous infusion, suppositories and oral administration thereof, as well as topical application of the compounds and compositions to the afflicted situs.

By "topical application" herein is meant directly laying on or spreading the compounds and compositions on epidermal tissue (including outer skin and oral, gingival, nasal, etc., tissue).

By "afflicted situs" herein is meant a localized area of inflammation, and the immediate surrounding area.

The process of the present invention is most conveniently carried out by administering compositions comprising both a phosphonate compound and a compatible salicylate compound and, optionally, compatible carrier materials.

By the term "comprising" as used herein is meant that various other, compatible drugs and medicaments, as well as inert ingredients, can be conjointly employed in the compositions and processes of this invention, as long as the critical phosphonate compounds and salicylate-based anti-inflammatory compounds are used in the manner disclosed. The term "comprising" thus encompasses and includes the more restrictive terms "consisting of" and "consisting essentially of" which characterize the use of the essential phosphonate compounds and salicylate compounds.

By "compatible" herein is meant that the components of the compositions are capable of being commingled without interacting in a manner which would substantially decrease the efficacy of the total compositions under ordinary use situations.

By "carrier" herein is meant a liquid, fluid or solid material which can optionally be used to provide finished compositions for systemic or topical administration of the drug compounds.

All percentages herein are by weight, unless otherwise specified.

The phosphonate compounds and salicylate compounds critical to the practice of this invention are described more fully hereinafter. Optional ingredients which can be included in the compositions to provide aesthetic, cosmetic, and convenience benefits, but which are not critical to the practice of the invention, are also disclosed.

The salicylate-based compounds used herein comprise salicylic acid, or derivatives thereof. Salicylic acid (o-hydroxybenzoic acid) is represented by the formula

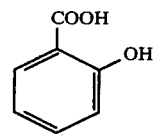

and can be derivatized at both the hydroxyl and carboxyl groups to provide various pharmacologically active analgesic and/or anti-inflammatory agents. The salicylate-based compounds employed in the practice of this invention are all well known in the medical arts and their anti-inflammatory activity in humans and lower animals is well documented.

Salicylic acid, its pharmaceutically-acceptable salts, and its pharmaceutically-acceptable esters and derivatives are used herein. Such materials include, for example, sodium salicylate, acetylsalicylic acid (aspirin; preferred herein), aloxiprin (a polymeric condensation product of aluminum oxide and aspirin), calcium carbaspirin (calcium acetylsalicylate-urea complex), choline salicylate ([2-hydroxyethyl]trimethylammonium salicylate), methyl salicylate, salicoside, salicylamide (o-hydroxybenzamide), acetylsalicylsalicylic acid, and salicylsulfuric acid. All of the foregoing materials are commercially available and are well-recognized for use as anti-inflammatory agents.

Other salicylic acid derivatives useful in the present compositions and which are especially useful for topical application to skin at a situs of inflammation, are of formula

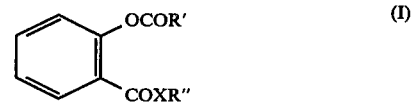

wherein R' is an alkyl substituent, especially alkyl having from 1 to 4 carbon atoms, X is O, NH or NR" and R" is a saturated or unsaturated aliphatic substituent having from 4 to 10 carbon atoms, benzyl or phenyl. The term "saturated or unsaturated aliphatic substituent" includes alkyl, alkenyl, alkadienyl, alkatrienyl, alkynyl and alkadiynyl groups.

The R" moiety can be unsubstituted or can be substituted with acetoxy; alkyloxy, e.g., methoxy, ethoxy and butoxy; alkylamido; halogen, e.g., chloro, bromo and fluoro; amino; nitro; alkyl, e.g., methyl, ethyl and butyl; amido; hydroxy and like groups without adversely affecting the overall efficacy of the salicylic acid derivative. Such groups can be in the ortho, meta or para positions when R" is benzyl or phenyl.

In general, the compounds of formula (I) are prepared from salicylic acid using standard organic synthetic techniques. In a representative synthesis scheme, salicylic acid is initially acylated with an appropriate acid anhydride of the formula $(R'CO)_2O$ wherein R' has from 1 to 4 carbon atoms. Examples of the anhydride are acetic anhydride, propionic anhydride, butyric anhydride, valeric anhydride and pivalyl anhydride. The reaction proceeds in the presence of sulfuric acid at a temperature from 40° C. to 80° C.

The resulting acyloxy benzoic acid is next reacted to form an ester (X=O) or an amide (X=NR"). Esterification is carried out by first reacting the acyloxy benzoic acid with oxalyl chloride or sulfonyl chloride to provide the corresponding acyloxy benzoyl chloride. This compound is then reacted with the appropriate alcohol in the presence of pyridine in standard fashion to provide the desired formula (I) ester. Examples of suitable alcohols include primary, secondary and tertiary -butanol, -pentanol, -hexanol, -heptanol and -octanol; unsaturated alcohols, e.g., 2-butenol, 2-hexenol, 4-hexenol, 2-octenol and 3-octenol; benzyl alcohol; and phenol.

The amide compounds of formula (I) are prepared by reacting the aforesaid acyloxy benzoyl chloride with the appropriate amine at a temperature of 0° C. to 30° C., in standard fashion. When a secondary amine of the formula HN(R")$_2$ is used, the two R" groups may be the same or different.

Preferred salicylic acid derivatives of formula (I) are those wherein X is oxygen (O). More preferred salicylic acid derivatives are those wherein X is O, R' is methyl or tertiary butyl, and R" is an alkyl group or benzyl. Highly preferred compounds are benzyl 2-acetoxybenzoate and hexyl 2-acetoxybenzoate.

The following compounds are exemplary salicylic acid derivatives of formula (I) suitable for use herein.

Butyl 2-acetoxybenzoate
Hexyl 2-acetoxybenzoate
2'-ethylhexyl 2-acetoxybenzoate
Octyl 2-acetoxybenzoate
Pentyl 2-propionoxybenzoate
Octyl 2-propionoxybenzoate
Hexyl 2-pivaloxybenzoate
Hexyl 2-butyroxybenzoate
2'-5'-Hexadienyl 2-acetoxybenzoate
2'-Hexenyl 2-acetoxybenzoate
Benzyl 2-butyroxybenzoate
Benzyl 2-acetoxybenzoate
Benzyl 2-pivaloxybenzoate
Phenyl 2-acetoxybenzoate
2-Acetoxy-N-hexylbenzamide
2-Propionoxy-N-octylbenzamide
2-Acetoxy-N,N-dibutylbenzamide
p-Acetamidophenyl 2-acetoxybenzoate
5'-Hydroxyhexyl 2-acetoxybenzoate
6'-Acetoxyhexyl 2-acetoxybenzoate
6'-Fluorohexyl 2-acetoxybenzoate
6'-Nitrohexyl 2-acetoxybenzoate
6'-Methylamidohexyl 2-acetoxybenzoate
2'-Ethyl-2'-5'-hexadienyl 2-acetoxybenzoate
2'-Acetoxybenzyl 2-propionoxybenzoate
2'-Fluorobenzyl 2-acetoxybenzoate
2'-Hydroxybenzyl 2-acetoxybenzoate
2'-Methoxybenzyl 2-acetoxybenzoate
2',4'-Diacetoxybenzyl 2-acetoxybenzoate
2'-Acetamidobenzyl 2-acetoxybenzoate The organophosphonate compounds (or, more succinctly, "phosphonates") employed in the manner of this invention are of the following type.

The phosphonate compounds which can be employed in the present invention are characterized by the phosphonate moiety (—PO$_3$M$_2$, wherein M represents H or a pharmaceutically-acceptable cation or ester group). The phosphonates herein are organophosphonates, i.e., the phosphonate moiety is attached to a carbon atom by a carbon-phosphorus bond (C—P bond). The carbon atom, in turn, can be bonded to other hydrocarbyl groups, e.g., alkyl phosphonates, or to hydrogen atoms, e.g., methane phosphonates, halogen atoms, e.g., dichloromethanediphosphonates, or to mixed hydrocarbyl groups, hydrogen atoms or other substituents, e.g., haloalkyl phosphonates. The hydrocarbyl groups can be substituted or non-substituted alkyl (including cycloalkyl), aryl (including heteroaryl) and the like. Substituent groups on the alkyl or aryl hydrocarbyl moiety can be, for example, additional phosphonate moieties; halogens, especially chlorine; carboxyl; esterified carboxyl; hydroxyl; amino; amido; and the like. Preferred for use herein are organophosphonates having more than one C—PO$_3$M$_2$ group; diphosphonates, especially geminal diphosphonates characterized by the grouping

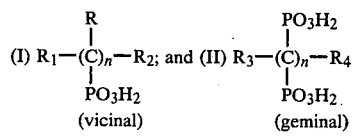

are most highly preferred.

Typical phosphonate compounds useful herein are of the formula

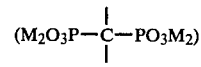

wherein n is an integer from 1 to about 10 and the substituent groups are H, alkyl, aryl, alkenyl, and the like. Examples of Type (I) phosphonates are those wherein R, R$_1$ and R$_2$ are each hydrogen, alkyl, —CH$_2$OH, or are as noted for groups R$_3$ and R$_4$. Examples of Type (II) phosphonates are those wherein R$_3$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., chlorine, bromine, and fluorine), amino, substituted amino (e.g., dimethylamino, diethylamino, N-hydroxy-N-ethylamino, acetylamino), —CH$_2$COOH, —CH$_2$PO$_3$H$_2$, —CH(PO$_3$H$_2$)(OH) or —CH$_2$CH(PO$_3$H$_2$)$_2$; R$_4$ is hydrogen, lower alkyl (e.g., methyl, ethyl, propyl, and butyl), amino, benzyl, halogen (e.g., chlorine, bromine and fluorine), hydroxyl, —CH$_2$COOH, —CH$_2$PO$_3$H$_2$, or —CH$_2$CH$_2$PO$_3$H$_2$, or a pharmaceutically-acceptable salt thereof such as alkali metal (e.g., sodium and potassium alkaline earth metal (e.g., calcium and magnesium), non-toxic heavy metal (e.g., stannous and indium), and ammonium or low molecular weight substituted ammonium (e.g., mono-, di-, and tri-ethanolammonium) salts. It will be appreciated that groups R, R$_1$ and R$_2$ and groups R$_3$ and R$_4$ can be cycloalkyl, heterocyclic or can be joined in ring structures, said rings being carbocyclic or heterocyclic.

The above-described organophosphonic acids and their pharmaceutically-acceptable salts and esters are commonly referred to collectively as "phosphonates", "diphosphonates" or "polyphosphonates".

Non-limiting examples of phosphonates of the above Type (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid; nonane- 1,2,3,4,5,6,7,8,9-nonaphosphonic acid; decane-1,2,3,4,5,6,7,8,9,10-decaphosphonic acid; and the pharmaceutically-acceptable salts of these acids, e.g., sodium, potassium, calcium, magnesium, ammonium, triethanolammonium, diethanolammonium, and monoethanolammonium salts.

Among the operable phosphonates encompassed by the above Type (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-nephthyl-1,1-diphosphonic acid; methanephenyldiphosphonic acid; ethane-1-amino-1,1-diphosphonic acid; dichloromethanediphosphonic acid (a.k.a. dichloromethylenediphosphonic acid and methanedichlorodiphosphonic acid); nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphonoprop-2-ene; octane-1,1-diphosphonic acid; dodecane-1,1-diphosphonic acid; phenylaminomethanediphosphonic acid; nephthylaminomethanediphosphonic acid; N,N-dimethylaminomethanediphosphonic acid; N-(2-hydroxyethyl)-aminomethanediphosphonic acid; N-acetylaminomethanediphosphonic acid; aminomethanediphosphonic acid; and the pharmaceutically-acceptable salts of these acids, e.g., sodium, potassium, calcium, magnesium, stannous, indium, ammonium, triethanolammonium, diethanolammonium, and monoethanolammonium salts.

Mixtures of any of the foregoing phosphonic acids and/or salts can be used in the practice of this invention.

The geminal diphosphonates of Type (II) are most preferred for use herein.

Ethane-1-hydroxy-1,1-diphosphonic acid is a preferred geminal diphosphonate for use herein. This compound has the molecular formula $CH_3C(OH)(PO_3H_2)_2$ (according to nomenclature by radicals, the acid may also be named 1-hydroxyethylidene diphosphonic acid). The most readily crystallizable salt of this acid is obtained when two or three of the acid hydrogens are replaced by sodium. Preferred salts for the purpose of this invention are the trisodium hydrogen salt and the disodium dihydrogen salt, and/or mixtures thereof.

Dichloromethanediphosphonic acid is an especially preferred geminal diphosphonate for use herein. This compound has the molecular formula $Cl_2C(PO_3H_2)_2$, abbreviated $Cl_2MDP$. The dichloromethanediphosphonates, especially the sodium salts of $Cl_2MDP$, are readily prepared and are most preferred for use in the practice of this invention.

The preparation of typical phosphonate compounds of the type disclosed for use herein is found in standard references and publications, especially the following.

Methanehydroxydiphosphonic acid and related compounds operable herein can be prepared, for example, by the reaction of phosgene with an alkali metal dialkylphosphite. A complete description of these compounds and the method for preparing same is found in U.S. Pat. No. 3,422,137, O. T. Quimby, incorporated herein by reference.

Ethane-1-hydroxy-1,1-diphosphonic acid can be prepared as disclosed in U.S. Pat. No. 3,400,149, incorporated herein by reference.

Methanediphosphonic acid and related compounds useful herein are described in detail in U.S. Pat. No. 3,213,030, granted Oct. 19, 1965; a preferred method of preparing such compounds is disclosed in U.S. Pat. No. 3,251,907, granted May 17, 1966, incorporated herein by reference.

Ethane-1,1,2-triphosphonic acid and related compounds which can be used in this invention, as well as a method for their preparation, are fully described in U.S. Pat. No. 3,551,339, O. T. Quimby, incorporated herein by reference.

Propane-1,1,3,3-tetraphosphonic acid and related compounds useful herein, and a method for preparing same are fully disclosed in U.S. Pat. No. 3,400,176, O. T. Quimby, incorporated herein by reference.

Pentane-2,2-diphosphonic acid and related compounds can be prepared in accordance with the method described by G. M. Kosolopoff in *J. Amer. Chem. Soc.* 75, 1500 (1953), incorporated herein by reference.

Propane-1,2,3-triphosphonic acid and salts thereof can be prepared by a process disclosed in U.S. Pat. No. 3,743,688, D. Allan Nicholson and Darrel Campbell, incorporated herein by reference.

Butane-1,2,3,4-tetraphosphonic acid and salts thereof can be prepared by a process disclosed in U.S. Pat. No. 3,755,504, D. Allan Nicholson and Darrel Campbell, incorporated herein by reference.

The higher aliphatic vicinal polyphosphonates and salts thereof can be prepared by the process disclosed in U.S. Pat. No. 3,584,035, Nicholson and Campbell, incorporated herein by reference.

Substituted ethane diphosphonic acids and salts and esters thereof are disclosed in U.S. Pat. No. 3,940,436, issued Feb. 24, 1976, to A. F. Kerst, the disclosures of which are incorporated herein by reference. U.S. Pat. No. 3,944,599, to the same inventor, discloses geminal diphosphonate compounds having halogen and hydroxyl substituent groups, and the means for preparing same. The disclosures of this patent are also incorporated herein by reference.

Phosphonobutane tri- and tetra-carboxylic acid compounds and their preparation are disclosed in U.S. Pat. Nos. 3,886,204 and 3,886,205, both issued May 27, 1975, to Geffers, et al., the disclosures of which are incorporated herein by reference.

German 2360-798, June 26, 1975, to Henkel & Cie GmbH discloses pharmaceutical and cosmetic preparations for influencing the deposition of poorly soluble calcium salts, said preparations comprising polymethylene phosphonic acid compounds. This publication, the disclosures of which are incorporated herein by reference, describes the preparation of the phosphonate materials in detail.

The preparation and pharmacological properties of various amino phosphonate compounds are described in German 2343-146 (Mar. 6, 1975); Belgian 822-930 (June 4, 1975); Belgian 822,929 (Dec. 6, 1973); German 2360-711 (June 12, 1975); German 2360-719 (June 6, 1975); Belgian 819-187 (Feb. 26, 1975); Belgian 819-188 (Feb. 26, 1975); and Belgian 819-189 (Feb. 26, 1975), the disclosures of said publications being incorporated herein by reference.

While any pharmaceutically-acceptable salt of the phosphonates can be used in the practice of this invention, the sodium salts are preferred. Various pharmaceutical cations such as potassium, ammonium, mono-, di-, and tri-ethanolammonium, and mixtures thereof, are also suitable for use as counterions in the salts, provided caution is observed in regulating the total intake of cation species in the salt composition. Such salts can be prepared by any suitable method involving neutralization of the parent phosphonic acid.

As can be seen from the foregoing, the preparation of the phosphonates used in the practice of this invention can be accomplished using well-known methods, or by simple modifications of various art-disclosed procedures. Only those organophosphonates which are pharmaceutically-acceptable (i.e., provide a satisfactory benefit:risk ratio) are contemplated for use herein. The well-known toxicity of some Type (I) monophosphonates ($n=1$) disclosed in the structural formulas above precludes their use herein. However, such materials are known in the art and are easily avoided in the practice of this invention.

Animal Tests

The following is an evaluation of the anti-inflammatory effects of ethane-1-hydroxy-1,1-diphosphonate (EHDP), dichloromethanediphosphonate (Cl$_2$MDP) and these compounds in combination with aspirin in a living animal system. The animal system makes use of an induced arthritis-like condition and has been recognized as a predictive tool for responses to anti-inflammatory compositions in humans.

Two hundred and thirty-five male Sprague Dawley rats (160–190 grams, Sprague Dawley Company, Madison, Wisconsin) were randomly allocated into 16 groups, allowed 1 week to adapt to their environment and then received the treatments set forth in Table I.

Arthritis responses were induced on the first day of the experiment by a single subcutaneous injection of Modified Freund's Adjuvant ("MFA", mineral oil containing *Mycobacterium butyricum*) into the distal third of the tail. The MFA was prepared to contain 8 mg of *M. butyricum* (Difco Laboratories, Detroit, Michigan) per ml of mineral oil (U.S. Pat. No. 185, Boron Oil Co., Cleveland, Ohio) and the resulting mixture was thoroughly stirred at high speed (Omni Mixer, Sorvol Co., Newtown, Connecticut) for 45 minutes prior to use. This mixture was kept under constant stirring at the time of administration. The MFA was administered according to body weight; dose volumes ranged from 0.09 ml for animals in the 153–170 g weight range to 0.15 ml for animals in the 261–280 g weight range.

Aspirin (Mallinckrodt, St. Louis, Missouri) was mixed with 0.5% methyl cellulose (Matheson, Norwood, Ohio) and a suspension prepared with a high speed mixer (Omni Mixer). These suspensions were administered at ½ ml/100 gram of body weight and were kept under constant stirring to insure homogeneity.

EHDP and Cl$_2$MDP were given as solutions adjusted to pH 7.4 with sodium hydroxide. Solution concentrations were adjusted so that a constant volume of 2 ml/kg could be maintained for animals receiving subcutaneous treatments. The solutions were prepared in 0.9% saline when the concentration was below 1.0% and in distilled water when above 1.0% (see Table I).

EHDP and Cl$_2$MDP were given once daily, beginning with the first day of the experiment, by subcutaneous injection at varying sites along the animal's back. Aspirin suspensions were also given once daily beginning on the first day by gastric intubation. In groups receiving both aspirin and the phosphonates, treatments were separated by a 4-hour interval to limit any possible influence of one compound on the absorption of the other.

The experiment was conducted over an 8-week period. The animals were housed individually and allowed free access to tap water and food (Purina Lab Chow, Ralston Purina Co., St. Louis, Mo.). Arthritis responses were followed grossly, radiographically and by measuring pedal edema at 1–2 week intervals. Pathologic mineralization which became radiographically apparent in arthritic extremities was measured using a grid system to assess the relative area of involvement. Bone resorption occurring in arthritic extremities was also assessed radiographically and given a rating from 0 to 3 according to severity (0=no resorption and 3=severe resorption) using standard examples of each severity grade. Pedal edema was measured by a standard method, involving the displacement of liquid.

TABLE I

| Group | Number of Animals | Treatment |
|---|---|---|
| I | 15 | Modified Freund's Adjuvant (MFA) + 0.5 mg P/kg/day EHDP given subcutaneously (sc) (0.10% solution in 0.9% saline) |
| II | 15 | MFA + 1 mg P/kg/day EHDP sc (0.21% solution in saline) |
| III | 15 | MFA + 2 mg P/kg/day EHDP sc (0.41% solution in saline) |
| IV | 15 | MFA + 4 mg P/kg/day EHDP sc (0.82% solution in saline) |
| V | 15 | MFA + 0.5 mg P/kg/day Cl$_2$MDP sc (0.12% solution in saline) |
| VI | 15 | MFA + 1 mg P/kg/day Cl$_2$MDP sc (0.23% solution in saline) |
| VII | 15 | MFA + 2 mg P/kg/day Cl$_2$MDP sc (0.46% solution in saline) |
| VIII | 15 | MFA + 4 mg/kg/day Cl$_2$MDP sc (0.93% solution in saline) |
| IX | 15 | MFA + 8 mg P/kg/day Cl$_2$MDP sc (1.86% aqueous solution) |
| X | 15 | MFA + 200 mg/kg/day aspirin given orally po (4% solution) |
| XI | 15 | MFA + 0.5 mg P/kg/day EHDP sc + 200 mg/kg/day aspirin po |
| XII | 15 | MFA + 1 mg P/kg/day EHDP sc + 200 mg/kg/day aspirin po |
| XIII | 15 | MFA + 0.5 mg P/kg/day Cl$_2$MDP sc + 200 mg/kg/day aspirin po |
| XIV | 15 | MFA + 1 mg P/kg/day Cl$_2$MDP sc + 200 mg/kg/day aspirin po |
| XV | 15 | MFA + saline sc |
| XVI | 10 | Non-treated control |

In Table I, phosphonate levels are expressed as milligrams phosphorus per kilogram of body weight per day (mg P/kg/day) so the test compounds can be compared on a molecular weight basis. Phosphonate solutions were adjusted for minor impurities.

A. Incidence of Arthritis

Inflammation became apparent in tails of all animals 24–48 hours after injection with MFA. This response then subsided for about 4 to 6 days and then began to flare and spread along the tail 10–12 days after MFA was administered. At this point, the animals became febrile and showed evidence of pain and inflammation in their extremities. There were no indications that any of the treatments had an effect on either the rate of onset or the incidence of this inflammatory reaction.

B. Paw Volumes

Both EHDP and $Cl_2MDP$ effectively inhibited pedal edema (as measured by changes in paw volumes) at almost every dose level from week 3 until the experiment was completed. In addition, at every dose level the paw volumes of the diphosphonate-treated animals became smaller as a function of time while those of saline controls continued to become larger. At dose levels of 0.5 and 1 mg P/kg/day, $Cl_2MDP$ appeared to be more effective than EHDP at inhibiting pedal edema, but the effectiveness of $Cl_2MDP$ did not show much further improvement with the higher dose levels. On the other hand, the response in animals given EHDP improved with increasing dose levels, so the two phosphonates appeared equally effective at the higher dose levels.

In the early stages of the experiment, aspirin appeared to be more effective than either of the phosphonates at inhibiting pedal edema, but as the experiment progressed most phosphonate-treated groups had paw volumes smaller than the group receiving aspirin.

When the phosphonates and aspirin were given as concomitant treatment, there appeared to be an additive effect, in that the paw volumes were almost always numerically, and in some cases significantly, ($P<0.05$) smaller than those of the groups receiving similar levels of the compounds given alone. Both phosphonates appeared equally effective in this respect.

C. Radiographic Changes

(1) Pathologic Bone Resorption

Both phosphonates significantly ($P<0.05$) inhibited pathologic bone resorption throughout the experimental period at all dose levels. At levels of 0.5 and 1 mg P/kg/day, $Cl_2MDP$ appeared to be more effective than EHDP while at higher levels the two phosphonates appeared equally effective.

Aspirin was also significantly ($P<0.05$) effective at inhibiting bone resorption, but at almost every dose level and time interval the phosphonates were more effective.

The combination of EHDP and aspirin also appeared to produce an additive effect on this response in that bone resorption in several instances was significantly ($P<0.05$) less severe in groups receiving aspirin-+EHDP than in groups receiving similar levels of either compound given alone. A similar effect was also observed in the group receiving 0.5 mg P/kg/day $Cl_2MDP$+aspirin while the response appeared slightly more severe in the group receiving 1 mg P/kg/day $Cl_2MDP$+aspirin when compared to the same level of $Cl_2MDP$ given alone. It is possible that there was a slight negative interaction between the higher level of $Cl_2MDP$ and aspirin but at any rate the response was still significantly ($P<0.05$) improved over aspirin given alone.

(2) Pathologic Mineralization

Both phosphonates also significantly inhibited pathologic mineralization at all intervals and at all dose levels. $Cl_2MDP$ again appeared slightly more effective at the 0.5 and 1 mg P/kg/day levels when all time periods were considered. At the 2 mg P/kg/day level, the phosphonates appeared equally effective while at 4 mg P/kg/day EHDP was clearly more effective and totally blocked the response at 6 and 8 weeks.

Aspirin was particularly effective at inhibiting this response and in fact appeared to be equal-to-or-better-than the phosphonates except at the 4 mg P/kg/day level of EHDP.

In every case the combination of aspirin and phosphonates resulted in a numerical improvement in pathologic mineralization over similar levels of the compounds given alone, but because of the variability of this response none of the differences were statistically ($P<0.05$) different.

D. Body Weights

Administration of MFA appeared to interfere with normal weight gain patterns of all animals participating in this study. Depending on the treatment group, the animals either gained very little or showed a net loss of body weight during the first 3–4 weeks. During the final 5–8 weeks, some recovery occurred. During the 8-week period, the average weight gain of the non-treated control animals was significantly ($P<0.05$) larger than any group receiving MFA.

Depending on the dose level administered, both phosphonates and aspirin significantly ($P<0.05$) inhibited the disturbance in body weight gains which appeared characteristic of this model. Aspirin appeared to be slightly more effective in this respect. During the periods when the disturbance in body weights was most apparent (weeks 2–4), the animals given $Cl_2MDP$ generally gained more weight as the dose levels were increased. The animals given EHDP appeared to show the same response until a level of 2 mg P/kg/day was reached, and then at 4 mg P/kg/day, the weight gain appeared to drop considerably. It is quite possible that the apparent lack of effect in this group is due to an overriding effect of EHDP, which has previously been shown to slow weight gain patterns in the rat at levels in this range.

When EHDP and aspirin were given as concomitant treatments, the effect on body weight gains appeared even more pronounced; however, the differences were not large enough to show a statistically significant improvement ($P<0.05$) over aspirin given alone. The combination of $Cl_2MDP$ and aspirin also showed an improvement over similar levels of $Cl_2MDP$ given alone, but when compared to the aspirin group, the weight gains appeared quite similar.

To summarize the results from the Animal Tests: Based on several criteria (body weight gain, pedal edema and bond resorption and calcification) the foregoing experiments clearly demonstrate that both of the foregoing, typical diphosphonate compounds and aspirin, when given alone, are effective in treating the inflammatory response in MFA-treated rats. Moreover, when the aspirin and the diphosphonates are administered in the same treatment regimen, an improved response is obtained, thus demonstrating that the diphosphonates potentiate the salicylate response. While not intending to be limited by theory, this improved response may be attributable to the fact that the diphosphonates and salicylates mediate the inflammatory response by entirely different mechanisms, with an overall improvement in net benefits when using combination therapy of the present type.

The present invention is most conveniently practiced by administering compositions which comprise mixtures of the salicylate-based anti-inflammatory agent and the phosphonate agent. In an alternate mode, a dosage regimen can consist of separate administration of the two types of agents, but this is less convenient.

Compositions comprising the salicylate-based anti-inflammatory agent and the phosphonate compound can be administered parenterally in aqueous solution by subcutaneous, intradermal, intramuscular or intravenous injection.

When administered orally, the phosphonate compounds herein are only about 10% absorbed through the gut, the rest being excreted. Accordingly, oral compositions typically contain an excess of the phosphonate material over that which can be effectively used in an injectable form to account for the low absorption.

Especially useful compositions herein for oral administration comprise, in unit dosage form, from about 10 mg to about 500 mg of acetylsalicylic acid and from about 50 mg to about 250 mg of dichloromethanediphosphonic acid, or a pharmaceutically-acceptable salt thereof. Similarly, oral compositions in unit dosage form comprising from about 10 mg to about 500 mg of acetylsalicylic acid and from about 50 mg to about 250 mg of ethane-1-hydroxy-1,1-diphosphonic acid, or a pharmaceutically-acceptable salt thereof, or methanediphosphonic acid, or a pharmaceutically-acceptable salt thereof, are useful in the practice of the invention.

Of course, the total daily usage of the compositions herein will be decided by the attending physician and will be determined by such factors as the type of inflammation being treated, the age and weight of the patient, the severity of the inflammation, and like factors well known in the medical arts. In general, treatment regimens according to the present invention comprise administering to an animal in need of such treatment from about 50 mg to about 6000 mg (preferably 100–1000 mg) of aspirin per day and from about 200 mg to about 2000 mg per day of the diphosphonates herein, especially dichloromethanediphosphonic acid, ethane-1-hydroxy-1,1-diphosphonic acid, methanediphosphonic acid, or the pharmaceutically-acceptable salts or esters of these respective acids; the dichloromethanediphosphonates are particularly useful herein as evidenced by the animal data and by virtue of their safety.

For purposes of oral administration, compositions can be formulated as capsules, tablets or granules. For treatment of non-human animals, compositions are preferably incorporated in animal feeds, feed supplements or feed concentrates.

Compositions comprising the salicylate-based anti-inflammatory agent and phosphonate can be administered, per se, or, more preferably, in combination with a solid or liquid filler, diluent or encapsulating substance as a pharmaceutical carrier, e.g., materials commonly used in the manufacture of tablets, capsules, elixirs, suppositories, and the like. Some examples of the substances which can serve as pharmaceutical carriers herein include pyrogen-free water; water-alcohol mixtures; saline; sugars such as lactose, glucose and sucrose; starches such as corn starch and potato starch; cellulose and its derivatives, such as sodium carboxymethylcellulose, ethylcellulose, cellulose acetate; powdered gums; malt; gelatin; stearic acid; calcium sulfate; vegetable oils, such as peanut oil and cottonseed oil; mineral oil; polyols such as propylene glycol, glycerin, sorbitol, mannitol and polyethylene glycol; agar; alginic acid; as well as other non-toxic, compatible substances used in pharmaceutical formulations. Wetting agents and lubricants such as sodium lauryl sulfate, as well as coloring agents, flavoring agents and preservatives can also be present.

For topical application directly to the afflicted situs, the compositions herein are preferably formulated as solutions in a liquid or semi-liquid carrier. Carriers which promote penetration of the present compositions into and through the skin to the subdermal, inflamed tissues are preferred in such topical compositions. The organic sulfoxides and phosphine oxides and mixtures thereof with sugar esters, and liquid and semi-liquid carriers comprising same, which are preferred for use with the present compositions are fully described in U.S. Pat. Nos. 3,903,256 and 3,839,566, MacMillan and Lyness, and U.S. Pat. Nos. 3,896,238 and 3,952,099, Smith, the disclosures of which are incorporated herein by reference.

Topical compositions herein generally comprise from about 1% to about 20% of the salicylate-based compound, from about 1% to about 20% of the phosphonate compound, the balance comprising a compatible carrier, usually a liquid or cream. Especially effective carriers comprise a $C_{10}$, or higher, organic sulfoxide compound to enhance penetration by the active drug agents. Decyl methyl sulfoxide (0.1%–10% of the topical composition) is especially useful for enhancing penetration of the drug agents through skin.

The compositions herein can be prepared by standard formulation and tableting techniques used in the pharmaceutical industry.

The following examples illustrate the present compositions and their use, but are not intended to be limiting of the scope of the invention.

EXAMPLE I

Capsules are prepared by conventional methods, as follows:

| Ingredient | mg. per capsule |
|---|---|
| Ethane-1-hydroxy-1,1-diphosphonic acid | 100 |
| Acetylsalicyclic acid | 300 |

Two capsules of the above type are administered orally four times daily to substantially reduce the pain and inflammation associated with arthritis, rheumatism, bursitis and lumbago.

In the composition of Example I, the ethane-1-hydroxy-1,1-diphosphonic acid is replaced by ethane-1-hydroxy-1,1-diphosphonic acid, sodium salt form, and equivalent results are secured.

In the capsules of Example I, the acetylsalicylic acid (aspirin) is replaced by an equivalent amount of sodium salicylate, aloxiprin, calcium carbaspirin, choline salicylate, methyl salicylate, salicoside, salicylamide, acetylsalicylsalicylic acid and salicylsulfuric acid, respectively, and equivalent results are secured.

EXAMPLE II

Capsules are prepared by conventional methods, as follows:

| Ingredient | mg. per capsule |
|---|---|
| Dichloromethanediphosphonic acid | 100 |
| Acetylsalicyclic acid | 300 |

Two capsules of the above type are administered orally four times daily to substantially reduce the pain and inflammation associated with arthritis, rheumatism, bursitis and lumbago.

In the composition of Example II, the dichloromethanediphosphonic acid is replaced by dichloromethanediphosphonic acid, sodium salt form, and equivalent results are secured.

In the capsules of Example II, the acetylsalicylic acid (aspirin) is replaced by an equivalent amount of sodium salicylate, aloxiprin, calcium carbaspirin, choline salicylate, methyl salicylate, salicoside, salicylamide, acetylsalicylsalicylic acid and salicylsulfuric acid, respectively, and equivalent results are secured.

EXAMPLE III

A topical composition is prepared by blending the following ingredients:

| Ingredient | % by Wt. |
| --- | --- |
| Decyl methyl sulfoxide | 0.5 |
| Ethane-1-hydroxy-1,1-diphosphonic acid, disodium salt | 5.0 |
| Aspirin (commercial) | 10.0 |
| Water | Balance |

The composition of Example III is applied topically to the joints of animals and humans to reduce pathological calcification associated with arthritis-like conditions caused by stress at the joints.

In the composition of Example III, the diphosphonate material is replaced by an equivalent amount of dichloromethanediphosphonic acid, disodium salt, and equivalent results are secured.

In the topical composition of Example III, the aspirin is replaced by an equivalent amount of benzyl 2-acetoxybenzoate and hexyl 2-acetoxybenzoate, respectively, and equivalent results are secured.

EXAMPLE IV

A suppository suitable for human or animal use is prepared from the following ingredients:

| Ingredient | % by Wt. |
| --- | --- |
| Aspirin (commercial) | 10.0 |
| Dichloromethanediphosphonic acid, disodium salt | 10.0 |
| Cocoa butter | Balance |

The composition of Example IV is prepared by melting the cocoa butter base at a temperature of ca. 39° C. and adding the diphosphonate and aspirin materials to the melt, with blending, to provide a homogeneous system. The cocoa butter/phosphonate/aspirin melt is poured into molds of appropriate dimensions and allowed to solidify. The resulting product is a lubricious suppository, or the like, which melts at body temperature to release the phosphonate and aspirin drug agents to provide improved anti-inflammatory benefits.

An injectable composition is made by replacing the cocoa butter of Example IV with sterile, pyrogen-free water.

EXAMPLE V

A topical composition in gel form is as follows:

| Ingredient | % by Wt. |
| --- | --- |
| Oleyl alcohol | 1.0 |
| Propylene glycol | 19.0 |
| Benzyl 2-acetoxybenzoate | 2.0 |
| Dichloromethanediphosphonic acid | 2.0 |
| Triethanolamine | 0.5 |
| Ethanol | 57.0 |
| Carbopol 940* | 0.5 |
| Water | Balance |

*Carbopol 940 is a carboxy vinyl polymer available from the B. F. Goodrich Chemical Co.

The composition of Example V is applied topically to an afflicted situs of a human or lower animal to control inflammation of the skin and sub-dermal tissues.

What is claimed is:

1. A composition of matter for treating pain and inflammation in animal tissue, comprising from about 10 milligrams to about 500 milligrams of a salicylate-based anti-inflammatory compound selected from the group consisting of salicyclic acid, acetylsalicylic acid, aloxiprin, calcium carbaspirin, choline salicylate, methyl salicylate, salicoside, salicylamide, acetylsalicylsalicylic acid, salicylsulfuric acid, and pharmaceutically-acceptable salts and esters thereof, and from about 50 milligrams to about 250 milligrams of an organophosphonate compound selected from the group consisting of geminal organophosphonates of the formula

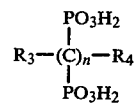

or pharmaceutically-acceptable salts thereof, wherein n is an integer from 1 to about 10; $R_3$ is selected from the group consisting of H, $C_1$–$C_{20}$ alkyl or cycloalkyl, $C_2$–$C_{20}$ alkenyl, aryl, phenylethyl, benzyl, halogen, amino, substituted amino, —$CH_2COOH$, —$CH_2(PO_3H_2)$, —$CH(PO_3H_2)(OH)$, or —$CH_2CH(PO_3H_2)_2$; and $R_4$ is selected from the group consisting of H, lower alkyl, amino, benzyl, halogen, —OH, —$CH_2COOH$, —$CH_2PO_3H_2$, or —$CH_2CH_2PO_3H_2$.

2. A composition according to claim 1 wherein the organophosphonate compound is a geminal diphosphonate.

3. A composition according to claim 2 wherein the organophosphonate compound is a member selected from the group consisting of ethane-1-hydroxy-1,1-diphosphonic acid, dichloromethanediphosphonic acid, methanediphosphonic acid, and the pharmaceutically-acceptable salts and esters thereof.

4. A composition according to claim 1, comprising a safe and effective amount of acetylsalicylic acid and a safe and effective amount of dichloromethanediphosphonic acid, or the pharmaceutically-acceptable salts or esters of said acids.

5. A composition according to claim 1, comprising a safe and effective amount of acetylsalicylic acid and a safe and effective amount of ethane-1-hydroxy-1,1-diphosphonic acid, or the pharmaceutically-acceptable salts or esters of said acids.

6. A composition according to claim 1, comprising a safe and effective amount of acetylsalicylic acid and a safe and effective amount of methanediphosphonic acid, or the pharmaceutically-acceptable salts or esters of said acids.

7. A composition of matter especially adapted for topical application to an afflicted situs to alleviate inflammation, comprising:
 (a) from about 1% to about 20% by weight of a salicylate-based anti-inflammatory compound selected from the group consisting of salicylic acid, acetylsalicylic acid, aloxiprin, calcium carbaspirin, choline salicylate, methyl salicylate, salicoside, salicylamide, acetylsalicylsalicylic acid, salicylsulfuric acid, benzyl 2-acetoxybenzoate, hexyl 2-acetoxybenzoate, and the pharmaceutically-acceptable salts and esters thereof;
 (b) from about 1% to about 20% by weight of a geminal organophosphonate compound having the formula

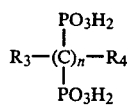

or pharmaceutically-acceptable salts and esters thereof, wherein n is an integer from 1 to about 10; $R_3$ is selected from the group consisting of H, $C_1$–$C_{20}$ alkyl or cycloalkyl, $C_2$–$C_{20}$ alkenyl, aryl, phenylethyl, benzyl, halogen, amino, substituted amino, —$CH_2COOH$, —$CH_2(PO_3H_2)$, —$CH(PO_3H_2)(OH)$, or —$CH_2CH(PO_3H_2)_2$; and $R_4$ is selected from the group consisting of H, lower alkyl, amino, benzyl, halogen, —OH, —$CH_2COOH$, —$CH_2PO_3H_2$, or —$CH_2CH_2PO_3H_2$; and
 (c) the balance comprising a compatible carrier.

8. A composition according to claim 7 wherein the organophosphonate compound is a geminal diphosphonate.

9. A composition according to claim 8 wherein the geminal diphosphonate is a member selected from the group consisting of ethane-1-hydroxy-1,1-diphosphonic acid, dichloromethanediphosphonic acid, methanediphosphonic acid, and the pharmaceutically-acceptable salts and esters thereof.

10. A composition according to claim 7 wherein the carrier comprises a safe and effective amount of a $C_{10}$, or higher, organic sulfoxide compound.

11. A composition according to claim 7 comprising a safe and effective amount of an anti-inflammatory compound selected from the group consisting of aspirin, benzyl 2-acetoxybenzoate and hexyl 2-acetoxybenzoate; a safe and effective amount of dichloromethanediphosphonic acid, or the pharmaceutically-acceptable salts thereof; the balance comprising a liquid, non-irritating carrier.

12. A composition according to claim 11 wherein the carrier comprises a safe and effective amount of decyl methyl sulfoxide.

13. A composition according to claim 1 or 5 wherein the salicylate-based anti-inflammatory agent is acetylsalicylic acid or a pharmaceutically-acceptable salt or ester thereof.

14. A method for treating or preventing pain and inflammation in animal tissues, comprising administering to an animal in need of such treatment from about 50 milligrams to about 6,000 milligrams per day of a salicylate-based anti-inflammatory compound selected from the group consisting of salicylic acid, acetylsalicylic acid, aloxiprin, calcium, carbaspirin, choline salicylate, methyl salicylate, salicoside, salicylamide, acetylsalicylsalicylic acid, salicylsulfuric acid, and pharmaceutically-acceptable salts and esters thereof, and from about 200 milligrams to about 2,000 milligrams per day of an organophosphonate compound selected from the group consisting of geminal organophosphonates of the formula

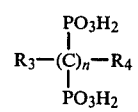

or pharmaceutically-acceptable salts thereof, wherein n is an integer from 1 to about 10; $R_3$ is selected from the group consisting of H, $C_1$–$C_{20}$ alkyl or cycloalkyl, $C_2$–$C_{20}$ alkenyl, aryl, phenylethyl, benzyl, halogen, amino, substituted amino, —$CH_2COOH$, —$CH_2(PO_3H_2)$, —$CH(PO_3H_2)(OH)$, or —$CH_2CH(PO_3H_2)_2$; and $R_4$ is selected from the group consisting of H, lower alkyl, amino, benzyl, halogen, —OH, —$CH_2COOH$, —$CH_2PO_3H_2$, or —$CH_2CH_2PO_3H_2$.

15. A method according to claim 14 wherein the organophosphonate compound is a geminal diphosphonate.

16. A method according to claim 15 wherein the organophosphonate compound is a member selected from the group consisting of ethane-1-hydroxy-1,1-diphosphonic acid, dichloromethanediphosphonic acid, methanediphosphonic acid, and the pharmaceutically-acceptable salts and esters thereof.

17. A method according to claim 14 wherein the animal is a human.

18. A method according to claim 17 which employs a safe and effective amount of aspirin and a safe and effective amount of dichloromethanediphosphonic acid, or the pharmaceutically-acceptable salts or esters thereof.

19. A method according to claim 17 which employs a safe and effective amount of aspirin and a safe and effective amount of ethane-1-hydroxy-1,1-diphosphonic acid, or the pharmaceutically-acceptable salts or esters thereof.

20. A method according to claim 17 which employs a safe and effective amount of aspirin and a safe and effective amount of methanediphosphonic acid, or the pharmaceutically-acceptable salts or esters thereof.

21. A method according to claim 14 or 16 wherein the salicylate-based anti-inflammatory agent is acetylsalicylic acid or a pharmaceutically-acceptable salt or ester thereof.

* * * * *